(12) United States Patent
Segall et al.

(10) Patent No.: US 11,503,842 B2
(45) Date of Patent: Nov. 22, 2022

(54) **PREPARATION OF NON-SOY OILSEED PROTEIN PRODUCTS ("*810")**

(71) Applicant: BURCON NUTRASCIENCE (MB) CORP., Winnipeg (CA)

(72) Inventors: Kevin I. Segall, Winnipeg (CA); Martin Schweizer, Winnipeg (CA); Brent E. Green, Warren (CA)

(73) Assignee: Burcon Nutrascience (MB) Corp., Winnipeg (CA)

( * ) Notice: Subject to any disclaimer, the term of this patent is extended or adjusted under 35 U.S.C. 154(b) by 55 days.

(21) Appl. No.: 16/071,653

(22) PCT Filed: Jan. 27, 2017

(86) PCT No.: PCT/CA2017/050092
§ 371 (c)(1),
(2) Date: Jul. 20, 2018

(87) PCT Pub. No.: WO2017/127934
PCT Pub. Date: Aug. 3, 2017

(65) Prior Publication Data
US 2019/0021363 A1 Jan. 24, 2019

Related U.S. Application Data

(60) Provisional application No. 62/287,532, filed on Jan. 27, 2016.

(51) Int. Cl.
*A23J 1/14* (2006.01)
*A23L 2/66* (2006.01)
(Continued)

(52) U.S. Cl.
CPC . *A23J 1/14* (2013.01); *A23J 3/14* (2013.01); *A23L 2/66* (2013.01); *A23L 33/185* (2016.08);
(Continued)

(58) Field of Classification Search
CPC . A23V 2002/00; A23V 2250/548; A23J 1/14; A23J 3/14; A23J 3/346; A23J 1/006;
(Continued)

(56) References Cited

U.S. PATENT DOCUMENTS

2014/0037824 A1 * 2/2014 Schweizer ......... B01D 11/0288
426/590

* cited by examiner

*Primary Examiner* — Hong T Yoo

(57) ABSTRACT

The present invention is directed to non-soy oilseed protein products, very low in, or free of, beany, green, vegetable or similar flavour notes and useful for the fortification of food and beverage products and prepared without the use of salt in the process. The non-soy oilseed protein products of the present invention are obtained by extracting non-soy oilseed protein source with water to form an aqueous non-soy oilseed protein solution, at least partially separating the aqueous non-soy oilseed protein solution from residual non-soy oilseed protein source, adjusting the pH of the aqueous non-soy oilseed protein solution to a pH between about 1.5 and a value about 1 pH unit lower than the typical pH of isoelectric precipitation to solubilize the bulk of the protein and form an acidified non-soy oilseed protein solution then separating the acidified non-soy oilseed protein solution from the acid insoluble solid material. The acidified non-soy oilseed protein solution may be dried following optional concentration and diafiltration to form a non-soy oilseed protein product, which may be an isolate. The acid insoluble solid material may be washed with acidified water and then dried to form another non-soy oilseed protein product. These products may be dried at the acidic pH at which they were prepared or may be adjusted in pH before drying.

61 Claims, 1 Drawing Sheet

(51) Int. Cl.
 *A23J 3/14* (2006.01)
 *A23L 33/185* (2016.01)
 *C12N 9/76* (2006.01)

(52) U.S. Cl.
 CPC .... *C12N 9/6427* (2013.01); *C12Y 304/21004* (2013.01)

(58) Field of Classification Search
 CPC ......... A23J 1/144; A23J 1/142; A23L 33/185; A23L 2/66
 See application file for complete search history.

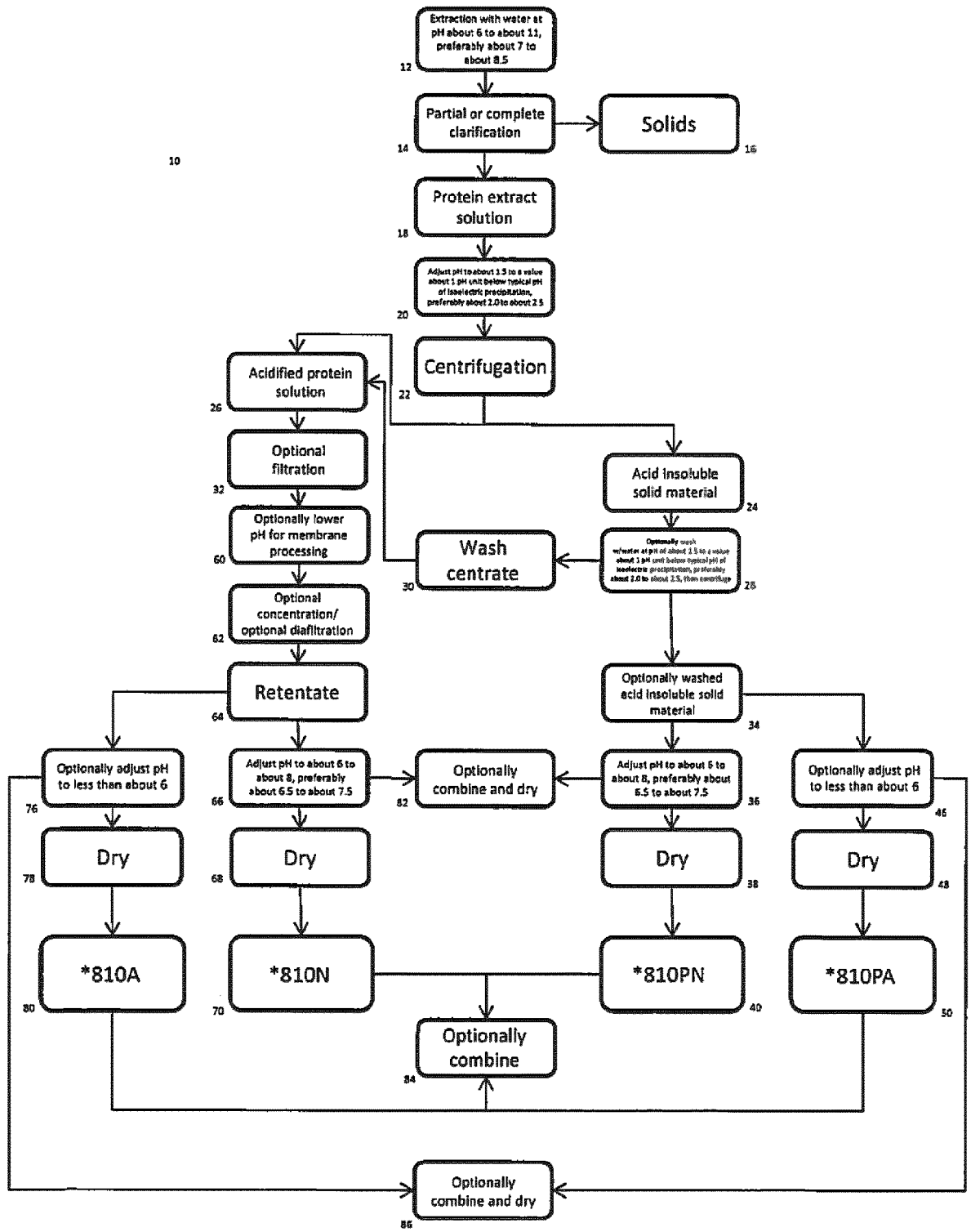

PREPARATION OF NON-SOY OILSEED PROTEIN PRODUCTS ("*810")

REFERENCE TO RELATED APPLICATION

This application is a U.S. National phase filing of PCT/CA2017/050092 filed Jan. 27, 2017 which itself claims priority of U.S. 62/287,532 filed Jan. 27, 2016.

FIELD OF THE INVENTION

The present invention relates to novel and inventive non-soy oilseed protein products and to novel and inventive methods of preparing non-soy oilseed protein products.

BACKGROUND TO THE INVENTION

In U.S. patent application Ser. No. 14/836,864, filed Aug. 27, 2015 (US Patent Publication No. 2016-0058031 published Mar. 3, 2016) assigned to the assignee hereof and the disclosures of which are incorporated herein by reference, there are described procedures for the preparation of novel and inventive soy protein products very low in, or substantially free of, beany flavour notes, and novel and inventive processes for the preparation thereof, which processes do not include the direct addition and use of calcium salt or other salt in extraction of the protein from the protein source material or in any other process step.

SUMMARY OF THE INVENTION

The present invention relates to novel and inventive oilseed protein products, other than soy protein products, very low in, or substantially free of, beany, green, vegetable or other similar off-flavour notes, and novel and inventive processes for the preparation thereof, which processes do not include the direct addition and use of calcium salt or other salt in extraction of the oilseed protein from the oilseed protein source material or in any other process step.

Accordingly, in one aspect of the present invention, there is provided a method of producing a non-soy oilseed protein product having a protein content of at least about 60 wt %, preferably at least about 90 wt % (N×6.25) on a dry basis, which method comprises:
  (a) extracting a non-soy oilseed protein source with water to cause solubilization of oilseed protein from the protein source and to form an aqueous non-soy oilseed protein solution,
  (b) at least partially separating the aqueous non-soy oilseed protein solution from the residual non-soy oilseed protein source,
  (c) adjusting the pH of the aqueous non-soy oilseed protein solution to between about 1.5 and a value about 1 pH unit below the typical pH of isoelectric precipitation to produce an acidified non-soy oilseed protein solution,
  (d) separating the acid insoluble solid material from the acidified non-soy oilseed protein solution,
  (e) optionally concentrating the acidified non-soy oilseed protein solution by a selective membrane technique,
  (f) optionally diafiltering the optionally concentrated acidified non-soy oilseed protein solution,
  (g) optionally drying the optionally concentrated and optionally diafiltered acidified non-soy oilseed protein solution.

In an embodiment of the present invention, when prepared at a low pH, the non-soy oilseed protein product of the present invention is well suited for use in food applications having a low pH.

In an embodiment of the present invention, the pH of the acidified non-soy oilseed protein solution or the optionally concentrated and optionally diafiltered acidified non-soy oilseed protein solution is raised to a value of less than about 8.0, prior to the optional drying step. In another embodiment of the present invention, the pH of the acidified non-soy oilseed protein solution or the optionally concentrated and optionally diafiltered acidified non-soy oilseed protein solution is raised to about 6.0 to about 8.0, prior to the optional drying step. In another embodiment of the present invention, the pH of the acidified non-soy oilseed protein solution or the optionally concentrated and optionally diafiltered acidified non-soy oilseed protein solution is raised to about 6.5 to about 7.5, prior to the optional drying step.

In an embodiment of the present invention, when the non-soy oilseed protein product is provided at neutral or near neutral pH, it is in a form suited for use in neutral or near-neutral food applications, such as neutral beverages or bars.

In an embodiment of the present invention, the acid insoluble solid material arising from the process of the present invention and collected as described in step (d) above is further processed to provide another non-soy oilseed protein product. This product may generally have lower purity and a higher level of off flavour notes compared to the products derived from the acidified non-soy oilseed protein solution. However, the purity and flavour of the product derived from the acid insoluble solid material is such that it is still suitable for use in food and beverage applications.

In an embodiment of the present invention, the acid insoluble solid material is optionally diluted then optionally dried to form a non-soy oilseed protein product having a protein content of at least about 60 wt % (N×6.25), on a dry weight basis.

In an embodiment of the present invention, the acid insoluble solid material is optionally diluted and then raised in pH to a value of less than about 8.0, prior to the optional drying step. In another embodiment of the present invention, the pH of the optionally diluted acid insoluble material is raised to about 6.0 to about 8.0, prior to the optional drying step. In another embodiment of the present invention, the pH of the optionally diluted acid insoluble material is raised to about 6.5 to about 7.5, prior to the optional drying step.

In an embodiment of the present invention, the acid insoluble solid material is washed by mixing with about 1 to about 20 volumes of water containing food grade acid to adjust the water to a pH selected from the group consisting of about 1.5 to a value about 1 pH unit lower than the typical pH of isoelectric precipitation and about the same as the pH of the acid insoluble solid material, then is separated from the wash water prior to optional dilution and the optional drying step. In another embodiment of the present invention, the acid insoluble solid material is washed by mixing with about 1 to about 10 volumes of water containing food grade acid to adjust the water to a pH selected from the group consisting of about 1.5 to a value about 1 pH unit lower than the typical pH of isoelectric precipitation and about the same as the pH of the acid insoluble solid material, then is separated from the wash water prior to optional dilution and the optional drying step.

In an embodiment of the present invention, the pH of the optionally diluted washed acid insoluble solid material is raised to a value of less than about 8.0, prior to the optional drying step. In another embodiment of the present invention, the pH of the optionally diluted washed acid insoluble solid material is raised to about 6.0 to about 8.0, prior to the optional drying step. In another embodiment of the present invention, the pH of the optionally diluted washed acid insoluble solid material is raised to about 6.5 to about 7.5, prior to the optional drying step.

In an embodiment of the present invention, the wash water is combined with the acidified non-soy oilseed protein solution of the separating step (d) and processed as in step (e), (f) and/or (g).

In an embodiment of the present invention, the acid insoluble solid material is simultaneously washed and adjusted in pH by mixing the acid insoluble solid material with about 1 to about 20 volumes of water and sufficient food grade alkali to raise the pH to the desired value, such as a value selected from the group of less than about 8.0 and between about 5.0 and about 8.0, then is separated from the wash water prior to optional dilution and the optional drying step. In another embodiment of the present invention, the acid insoluble solid material is simultaneously washed and adjusted in pH by mixing the acid insoluble solid material with about 1 to about 10 volumes of water and sufficient food grade alkali to raise the pH to the desired value, such as a value selected from the group of less than about 8.0 and between about 5.0 and about 8.0, then is separated from the wash water prior to optional dilution and the optional drying step. In another embodiment of the present invention, the separated washed and pH adjusted acid insoluble solid material may be optionally diluted and further raised in pH as to a value selected from the group of less than about 8.0, between about 6.0 and about 8.0 and between about 6.5 and about 7.5 and then optionally dried.

In an embodiment of the present invention, the optionally diluted, optionally washed and optionally pH adjusted acid insoluble solid material is pasteurized prior to drying.

In an embodiment of the present invention, the pasteurization step is effected at a temperature of about 55° to about 85° C. for about 10 seconds to about 60 minutes. In another embodiment of the present invention, the pasteurization step is effected at a temperature of about 60° to about 70° C. for about 10 minutes to about 60 minutes. In another embodiment of the present invention, the pasteurization step is effected at a temperature of about 70° to about 85° C. for about 10 seconds to about 60 seconds.

In an embodiment of the present invention, the extraction step (a) is effected at a temperature of about 1° to about 100° C. In another embodiment of the present invention, the extraction step (a) is effected at a temperature of about 15° to about 65° C. In another embodiment of the present invention, the extraction step (a) is effected at a temperature of about 50° to about 60° C.

In an embodiment of the present invention, the water used for the extraction contains a pH adjusting agent so that the extraction is conducted at a pH of about 6 to about 11. In another embodiment of the present invention, the water used for the extraction contains a pH adjusting agent so that the extraction is conducted at a pH of about 7 to about 8.5. In another embodiment of the present invention, the pH adjusting agent is sodium hydroxide, potassium hydroxide, or any other conventional food grade alkali and combinations thereof.

In an embodiment of the present invention, the water used for the extraction contains an antioxidant.

In an embodiment of the present invention, the aqueous non-soy oilseed protein solution arising from the separation step (b) has a protein concentration of about 5 to about 50 g/L. In another embodiment of the present invention, the aqueous non-soy oilseed protein solution has a protein concentration of about 10 to about 50 g/L.

In an embodiment of the present invention, following the separation step (b) and prior to the acidification step (c), the aqueous non-soy oilseed protein solution is treated with an adsorbent to remove colour and/or odour compounds from the aqueous protein solution.

In an embodiment of the present invention, following the separation step (b) and prior to the acidification step (c), the aqueous non-soy oilseed protein solution may optionally be adjusted in temperature to about 1 to about 35° C. In another embodiment, the temperature of the aqueous non-soy oilseed protein solution may optionally be adjusted to about 15 to about 35° C.

In an embodiment of the present invention, the pH of said non-soy aqueous oilseed protein solution is adjusted in the acidifying step (c) to about 2.0 to about 2.5.

In an embodiment of the present invention, the separation step (d) consists of a centrifugation step and/or a filtration step.

In an embodiment of the present invention, the acidified aqueous protein solution following separating step (d) is subjected to a heat treatment step. In an embodiment of the present invention, the heat treatment step is effected to inactivate heat-labile anti-nutritional factors. In an embodiment of the present invention, the anti-nutritional factors are heat-labile trypsin inhibitors. In another embodiment of the present invention, the heat treatment step is effected to pasteurize the acidified aqueous protein solution.

In an embodiment of the present invention, the heat treatment is effected at a temperature of about 70° to about 160° C. for about 10 seconds to about 60 minutes. In another embodiment of the present invention, the heat treatment is effected at a temperature of about 80° to about 120° C. for about 10 seconds to about 5 minutes. In another embodiment of the present invention, the heat treatment is effected at a temperature of about 85° to about 95° C. for about 30 seconds to about 5 minutes.

In an embodiment of the present invention, the heat treated acidified non-soy oilseed protein solution is cooled to a temperature of about 2° to about 65° C. In another embodiment of the present invention, the heat treated acidified non-soy oilseed protein solution is cooled to a temperature of about 50° to about 60° C.

In an embodiment of the present invention, the acidified aqueous non-soy oilseed protein solution is dried to provide a non-soy oilseed protein product having a protein content of at least about 60 wt % (N×6.25) d.b.

In an embodiment of the present invention, the acidified aqueous non-soy oilseed protein solution is subjected to concentrating step (e). In another embodiment of the present invention, the acidified aqueous non-soy oilseed protein solution is subjected to concentrating step (e) to produce a concentrated acidified non-soy oilseed protein solution having a protein concentration of about 50 to about 300 g/L.

In another embodiment of the present invention, the acidified aqueous non-soy oilseed protein solution is subjected to concentrating step (e) to produce a concentrated acidified non-soy oilseed protein solution having a protein concentration of about 100 to about 200 g/L.

In an embodiment of the present invention, the concentrating step (e) is effected by ultrafiltration using a membrane having a molecular weight cut-off of about 1,000 to about 1,000,000 daltons. In another embodiment of the present invention, the concentrating step (e) is effected by ultrafiltration using a membrane having a molecular weight cut-off of about 1,000 to about 100,000 daltons.

In an embodiment of the present invention, the acidified non-soy oilseed protein solution is subjected to diafiltering step (f). In an embodiment of the present invention, the diafiltration step (f) is effected using water or acidified water on the acidified aqueous non-soy oilseed protein solution in the absence of concentrating step (e) or before or after partial or complete concentration thereof.

In an embodiment of the present invention, the diafiltration step (f) is effected using about 1 to about 40 volumes of diafiltration solution. In another embodiment of the present invention, the diafiltration step (f) is effected using about 2 to about 25 volumes of diafiltration solution.

In an embodiment of the present invention, the diafiltration step (f) is effected until no significant further quantities of contaminants or visible colour are present in the permeate.

In an embodiment of the present invention, the diafiltration step (f) is effected until the retentate has been sufficiently purified so as to provide a non-soy oilseed protein isolate with a protein content of at least about 90 wt % (N×6.25) d.b.

In an embodiment of the present invention, the diafiltration step (f) is effected using a membrane having a molecular weight cut-off of about 1,000 to about 1,000,000 daltons. In another embodiment of the present invention, the diafiltration step (f) is effected using a membrane having a molecular weight cut-off of about 1,000 to about 100,000 daltons.

In an embodiment of the present invention, an antioxidant is present in the diafiltration medium during at least part of the diafiltration step (f).

In an embodiment of the present invention, the concentration step (e) and/or the diafiltration step (f) are carried out at a temperature of about 2° to about 65° C. In another embodiment of the present invention, the concentration step (e) and/or diafiltration step (f) are carried out at a temperature of about 50° to about 60° C.

In an embodiment of the present invention, the optionally partially or completely concentrated and optionally diafiltered acidified non-soy oilseed protein solution is subjected to a heat treatment step. In an embodiment of the present invention, the heat treatment step is effected to inactivate heat-labile anti-nutritional factors. In an embodiment of the present invention, the anti-nutritional factors are heat-labile trypsin inhibitors.

In an embodiment of the present invention, the heat treatment is effected at a temperature of about 70° to about 160° C. for about 10 seconds to about 60 minutes. In another embodiment of the present invention, the heat treatment is effected at a temperature of about 80° to about 120° C. for about 10 seconds to about 5 minutes. In another embodiment of the present invention, the heat treatment is effected at a temperature of about 85° C. to about 95° C. for about 30 seconds to about 5 minutes.

In an embodiment of the present invention, the heat treated non-soy oilseed protein solution is cooled to a temperature of about 2° to about 65° C. In another embodiment of the present invention, the heat treated non-soy oilseed protein solution is cooled to a temperature of about 50° to about 60° C.

In an embodiment of the present invention, the optionally concentrated and optionally diafiltered acidified protein solution is treated with an adsorbent to remove colour and/or odour compounds.

In an embodiment of the present invention, the optionally concentrated and optionally diafiltered acidified protein solution is pasteurized prior to drying.

In an embodiment of the present invention, the pasteurization step is effected at a temperature of about 55° to about 85° C. for about 10 seconds to about 60 minutes. In another embodiment of the present invention, the pasteurization step is effected at a temperature of about 60° to about 70° C. for about 10 minutes to about 60 minutes. In another embodiment of the present invention, the pasteurization step is effected at a temperature of about 70° to about 85° C. for about 10 seconds to about 60 seconds.

In an embodiment of the present invention, the optionally concentrated and optionally diafiltered acidified non-soy oilseed protein solution is subjected to drying step (g) to provide a non-soy oilseed protein isolate having a protein content of at least about 90 wt % (N×6.25) d.b. The Applicant has identified this non-soy oilseed protein isolate as *810, where the asterisk represents the abbreviation for the type of oilseed, e.g. C for canola, SF for sunflower, H for hemp, etc.

In an embodiment of the present invention, the pH of the optionally concentrated and optionally diafiltered acidified non-soy oilseed protein solution is raised to a value less than about 8.0, prior to optional drying step (g). In another embodiment of the present invention, the pH of the optionally concentrated and optionally diafiltered acidified non-soy oilseed protein solution is raised to about 6.0 to about 8.0, prior to optional drying step (g). In another embodiment of the present invention, the pH of the optionally concentrated and optionally diafiltered acidified non-soy oilseed protein solution is raised to about 6.5 to about 7.5, prior to optional drying step (g).

In an embodiment of the present invention, the optional concentration and/or optional diafiltration step are operated in a manner favourable to the removal of trypsin inhibitors.

In an embodiment of the present invention, a reducing agent is present during the extraction step (a). In an embodiment of the present invention, the reducing agent is selected from the group consisting of sodium sulfite, cysteine, N-acetylcysteine and combinations thereof. In an embodiment of the present invention, the presence of the reducing agent is intended to disrupt or rearrange the disulfide bonds of trypsin inhibitors to achieve a reduction in trypsin inhibitor activity. In another embodiment of the present invention, a reducing agent is present during the optional concentration step (e) and/or the optional diafiltration step (f). In an embodiment of the present invention, the reducing agent is selected from the group consisting of sodium sulfite, cysteine, N-acetylcysteine and combinations thereof. In an embodiment of the present invention, the presence of the reducing agent is intended to disrupt or rearrange the disulfide bonds of trypsin inhibitors to achieve a reduction in trypsin inhibitor activity.

In another embodiment of the present invention, a reducing agent is added to the optionally concentrated and optionally diafiltered non-soy oilseed protein solution prior to the drying step (g) and/or to the dried non-soy oilseed protein product. In an embodiment of the present invention, the reducing agent is selected from the group consisting of sodium sulfite, cysteine, N-acetylcysteine and combinations thereof. In an embodiment of the present invention, the presence of the reducing agent is intended to disrupt or rearrange the disulfide bonds of trypsin inhibitors to achieve a reduction in trypsin inhibitor activity.

In another embodiment of the present invention, there is provided a food product formulated to contain the non-soy oilseed protein product of the present invention. In an embodiment of the present invention, the food product is a beverage.

The non-soy oilseed protein products produced according to the processes of the present invention disclosed herein are suitable for use in a wide variety of conventional applications of protein products, including, but not limited to, protein fortification of processed foods and beverages and as functional ingredients in foods and beverages. Other uses of the non-soy oilseed protein products of the present invention are in pet foods, animal feed and in industrial and cosmetic applications and in personal care products.

BRIEF DESCRIPTION OF DRAWINGS

FIG. 1 is a schematic flow sheet of an embodiment of a process of the present invention.

GENERAL DESCRIPTION OF THE INVENTION

The initial step of the process of providing the non-soy oilseed protein products of the present invention involves solubilizing oilseed protein from a non-soy oilseed protein source. The non-soy oilseed protein source may be any oilseed excluding soy, including but not limited to canola, sunflower, hemp, safflower, cottonseed, flax, sesame, mustard and peanut or any oilseed product or by-product derived from the processing of non-soy oilseeds, including, but not limited to hull fractions from oilseed dehulling, oilseed meal and protein products derived from oilseed meal. The non-soy oilseed protein source may be used in the full fat form, partially defatted form or fully defatted form. Where the non-soy oilseed protein source contains an appreciable amount of fat, an oil removal step generally is required during the process. The non-soy oilseed protein recovered from the non-soy oilseed protein source may be the protein naturally occurring in the oilseed or the proteinaceous material may be a protein modified by genetic manipulation but possessing characteristic hydrophobic and polar properties of the natural protein.

The non-soy oilseed protein products of the present invention may be prepared from non-soy oilseed protein source by either a batch process or a continuous process or a semi-continuous process. Protein solubilization from the non-soy oilseed protein source material is effected using water. The water used may be tap water or water having different levels of purity. Reverse osmosis (RO) purified water is preferred.

The pH of the extraction may be about 6 to about 11, preferably about 7.0 to about 8.5. Food grade sodium hydroxide, potassium hydroxide or any other conventional food grade alkali and combinations thereof may be added to the water to adjust the pH of the extraction as required. Choice of extraction pH is influenced by the type of non-soy oilseed being processed. Lower extraction pH values are preferred for non-soy oilseed protein sources high in phenolics such as canola and sunflower. The solubilization of the protein is effected at a temperature of from about 1° to about 100° C., preferably about 15° to about 65° C., more preferably about 50° C. to about 60° C., preferably accompanied by agitation to decrease the solubilization time, which is usually about 1 to about 60 minutes. It is preferred to effect the solubilization to extract substantially as much protein from the non-soy oilseed protein source as is practicable, so as to provide an overall high product yield.

Extraction of the protein from the non-soy oilseed protein source, when conducted in a continuous operation, is carried out in any manner consistent with effecting a continuous extraction of protein from the non-soy oilseed protein source. In one embodiment, the non-soy oilseed protein source is continuously mixed with the water and the mixture is conveyed through a pipe or conduit having a length and at a flow rate for a residence time sufficient to effect the desired extraction in accordance with the parameters described herein.

The concentration of non-soy oilseed protein source in the water during the solubilization step may vary widely. Typical concentration values are about 5 to about 15% w/v.

The protein extraction step has the additional effect of solubilizing fats which may be present in the non-soy oilseed protein source, which then results in the fats being present in the aqueous phase.

The protein solution resulting from the extraction step generally has a protein concentration of about 5 to about 50 g/L, preferably about 10 to about 50 g/L.

The water of extraction may contain an antioxidant. The antioxidant may be any conventional antioxidant, such as sodium sulfite or ascorbic acid. The quantity of antioxidant employed may vary from about 0.01 to about 1 wt % of the solution, preferably about 0.05 wt %. The antioxidant may serve to inhibit oxidation of phenolics in the protein solution.

The aqueous phase resulting from the extraction step then may be separated from the bulk of the residual non-soy oilseed protein source, in any conventional manner, such as by employing a decanter centrifuge. Preferably, the finer residual non-soy oilseed protein source material is left in the non-soy oilseed protein solution, but if desired, these finer solids may be removed in any conventional manner, such as by disc centrifugation and/or filtration. The separation step may be conducted at the same temperature as the extraction step or at any temperature within the range of about 1° to about 100° C., preferably about 15° to about 65° C., more preferably about 50° to about 60° C. The separated residual non-soy oilseed protein source material may be dried for disposal or further processed, such as to recover residual protein. Residual protein may be recovered by re-extracting the separated residual non-soy oilseed protein source with fresh water and the protein solution yielded upon clarification combined with the initial protein solution for further processing as described below. A counter-current extraction procedure may also be utilized. The separated residual non-soy oilseed protein source may alternatively be processed by any other conventional procedure to recover residual protein.

The aqueous non-soy oilseed protein solution may be treated with an anti-foamer, such as any suitable food-grade, non-silicone based anti-foamer, to reduce the volume of foam formed upon further processing. The quantity of anti-foamer employed is generally greater than about 0.0003% w/v. Alternatively, the anti-foamer in the quantity described may be added in the extraction steps.

The separated aqueous non-soy oilseed protein solution may be subject to a defatting operation, if desired or required. Defatting of the separated aqueous non-soy oilseed protein solution may be achieved by any conventional procedure.

The aqueous non-soy oilseed protein solution may be treated with an adsorbent, such as granulated activated carbon, to remove colour and/or odour compounds. Such adsorbent treatment may be carried out under any conventional conditions, generally at the ambient temperature of the separated aqueous protein solution.

The non-soy oilseed protein solution is then adjusted in pH to a value between about 1.5 and a value which is about 1 unit below the pH at which isoelectric precipitation is typically performed. As the pH at which isoelectric precipitation is typically performed varies somewhat between different non-soy oilseeds, the pH range for the acidification step varies with the non-soy oilseed protein source. When the process is applied to canola, the pH is adjusted to a value between about 1.5 and about 2.5. When the process is applied to sunflower, the pH is adjusted to a value between about 1.5 and about 3.5. When the process is applied to hemp, the pH is adjusted to a value between about 1.5 and about 4.0. When the process is applied to cottonseed, the pH is adjusted to a value between about 1.5 and about 3.0. When the process is applied to flax/linseed, the pH is adjusted to a value between about 1.5 and about 3.0. When the process is applied to safflower, the pH is adjusted to a value between about 1.5 and about 4.0. When the process is applied to sesame, the pH is adjusted to a value between about 1.5 and about 3.0. When the process is applied to mustard, the pH is adjusted to a value between about 1.5 and about 4.0. When the process is applied to peanut, the pH is adjusted to a value between about 1.5 and about 3.5. In all cases, preferably the non-soy oilseed protein solution is adjusted in pH to about 2.0 to about 2.5. The pH adjustment is made by the addition of any conventional food grade acid, such as hydrochloric acid, phosphoric acid or any other conventional food grade acid and combinations thereof.

By adjusting the pH to lower values in the process of the present invention, a greater portion of the proteins, preferably a significant portion of the proteins, preferably about 60 wt % or more, more preferably about 80 wt % or more of the protein, is soluble in the acidified solution. The pH adjustment may be done at the temperature of the non-soy oilseed protein solution, or the temperature of the non-soy oilseed protein solution may be adjusted prior to pH adjustment such as to about 15° to about 35° C. If desired, the non-soy oilseed protein solution may be diluted with water prior to the acidification step described above.

The protein that is not soluble in the acidified protein solution is contained in what is termed the acid insoluble solid material, which is removed from the acidified non-soy oilseed protein solution by any conventional means, such as the use of a disc stack centrifuge and further processed as described below. The acidified protein solution may then be filtered by any conventional means such as using filter presses or by microfiltration to remove any fine acid insoluble solid material remaining in the acidified protein solution after the centrifugation step. Applying the filtration step may also reduce the fat content in the acidified protein solution.

If desired, the pH of the acidified protein solution may be lowered further prior to further processing. The adjusted pH of the acidified protein solution should still be in the range described above of about 1.5 to a value of about 1 unit below the typical pH of isoelectric precipitation, preferably about 2.0 to about 2.5.

The acidified aqueous non-soy oilseed protein solution may be subjected to a heat treatment to inactivate heat labile anti-nutritional factors, which may include trypsin inhibitors, present in such solution as a result of extraction from the non-soy oilseed protein source material during the extraction step. Such a heating step also provides the additional benefit of reducing the microbial load. Generally, the protein solution is heated to a temperature of about 70° to about 160° C., preferably about 80° to about 120° C., more preferably about 85° to about 95° C., for about 10 seconds to about 60 minutes, preferably about 10 seconds to about 5 minutes, more preferably about 30 seconds to about 5 minutes. The heat treated acidified non-soy oilseed protein solution then may be cooled for further processing as described below, to a temperature of about 2° to about 65° C., preferably about 50° C. to about 60° C.

The resulting acidified aqueous soy protein solution may be directly dried to produce a non-soy oilseed protein product. In order to provide a non-soy oilseed protein product having a decreased impurities content, such as a non-soy oilseed protein isolate, the acidified aqueous non-soy oilseed protein solution may be processed as described below prior to drying. Further processing as described below is also believed to have a beneficial effect on the flavour of the product.

The acidified aqueous non-soy oilseed protein solution may be concentrated to provide a concentrated non-soy oilseed protein solution having a protein concentration of about 50 to about 300 g/L, preferably about 100 to about 200 g/L.

The concentration step may be effected in any conventional manner consistent with batch or continuous operation, such as by employing any conventional selective membrane technique, such as ultrafiltration or diafiltration, using membranes, such as hollow-fibre membranes or spiral-wound membranes, with a suitable molecular weight cut-off, such as about 1,000 to about 1,000,000 daltons, preferably about 1,000 to about 100,000 daltons, having regard to differing membrane materials and configurations, and, for continuous operation, dimensioned to permit the desired degree of concentration as the aqueous protein solution passes through the membranes.

As is well known, ultrafiltration and similar selective membrane techniques permit low molecular weight species to pass therethrough while preventing higher molecular weight species from so doing. The low molecular weight species include low molecular weight materials extracted from the source material, such as carbohydrates, pigments, low molecular weight proteins and anti-nutritional factors, such as trypsin inhibitors, which are themselves low molecular weight proteins. The molecular weight cut-off of the membrane is usually chosen to ensure retention of a significant proportion of the protein in the solution, while permitting contaminants to pass through having regard to the different membrane materials and configurations.

The concentrated non-soy oilseed protein solution then may be subjected to a diafiltration step using water. The diafiltration water is preferably at a pH equal to that of the protein solution being diafiltered. Such diafiltration may be effected using from about 1 to about 40 volumes of diafiltration solution, preferably about 2 to about 25 volumes of diafiltration solution. In the diafiltration operation, further quantities of contaminants are removed from the aqueous non-soy oilseed protein solution by passage through the membrane with the permeate. This purifies the aqueous protein solution and may also reduce its viscosity. The diafiltration operation may be effected until no significant further quantities of contaminants or visible colour are present in the permeate or until the retentate has been sufficiently purified so as to provide a non-soy oilseed protein isolate with a protein content of at least about 90 wt % (N×6.25) d.b. Such diafiltration may be effected using the same membrane as for the concentration step. However, if desired, the diafiltration step may be effected using a separate membrane with a different molecular weight cut-off, such as a membrane having a molecular weight cut-off in the range of about 1,000 to about 1,000,000 daltons, preferably about 1,000 to about 100,000 daltons, having regard to different membrane materials and configuration.

Alternatively, the diafiltration step may be applied to the acidified aqueous protein solution prior to concentration or to partially concentrated acidified aqueous protein solution. Diafiltration may also be applied at multiple points during the concentration process. When diafiltration is applied prior to concentration or to the partially concentrated solution, the resulting diafiltered solution may then be additionally concentrated. Diafiltering multiple times as the protein solution is concentrated may allow a higher final, fully concentrated protein concentration to be achieved. This reduces the volume of material to be dried.

The concentration step and the diafiltration step may be effected herein in such a manner that the non-soy oilseed protein product subsequently recovered contains less than about 90 wt % protein (N×6.25) d.b., such as at least about 60 wt % protein (N×6.25) d.b. By partially concentrating and/or partially diafiltering the aqueous non-soy oilseed protein solution, it is possible to only partially remove contaminants. This protein solution may then be dried to provide a non-soy oilseed protein product with lower levels of purity.

An antioxidant may be present in the diafiltration water during at least part of the diafiltration step. The antioxidant may be any conventional antioxidant, such as sodium sulfite or ascorbic acid. The quantity of antioxidant employed in the diafiltration water depends on the materials employed and may vary from about 0.01 to about 1 wt %, preferably about 0.05 wt %. The antioxidant may serve to inhibit the oxidation of phenolics present in the non-soy oilseed protein solution.

The optional concentration step and the optional diafiltration step may be effected at any conventional temperature, generally about 2° to about 65° C., preferably about 50° to about 60° C., and for the period of time to effect the desired degree of concentration and diafiltration. The temperature and other conditions used to some degree depend upon the membrane equipment used to effect the membrane processing, the desired protein concentration of the solution and the efficiency of the removal of contaminants to the permeate.

As alluded to earlier, non-soy oilseeds can contain antinutritional trypsin inhibitors. The level of trypsin inhibitor activity in the final non-soy oilseed protein product can be controlled by the manipulation of various process variables.

As noted above, heat treatment of the acidified aqueous non-soy oilseed protein solution may be used to inactivate heat-labile trypsin inhibitors. The partially concentrated or fully concentrated acidified non-soy oilseed protein solution may also be heat treated to inactivate heat labile trypsin inhibitors. When the heat treatment is applied to the partially concentrated acidified non-soy oilseed protein solution, the resulting heat treated solution may then be additionally concentrated.

In addition, the concentration and/or diafiltration steps may be operated in a manner favourable for removal of trypsin inhibitors in the permeate along with the other contaminants. Removal of the trypsin inhibitors is promoted by using a membrane of larger pore size, such as 30,000 to 1,000,000 Da, operating the membrane at elevated temperatures, such as about 30° to about 65° C., preferably about 50° to about 60° C. and employing greater volumes of diafiltration medium, such as 10 to 40 volumes.

Acidifying and membrane processing the non-soy oilseed protein solution at a lower pH, such as 1.5 to 2.5, may reduce the trypsin inhibitor activity relative to processing the solution at higher pH, such as 2.5 to 4.0. When the protein solution is concentrated and/or diafiltered at the low end of the pH range, it may be desired to raise the pH of the solution prior to drying. The pH of the concentrated and/or diafiltered protein solution may be raised to the desired value, for example pH 3, by the addition of any conventional food grade alkali, such as sodium hydroxide, potassium hydroxide and combinations thereof.

Further, a reduction in trypsin inhibitor activity may be achieved by exposing non-soy oilseed materials to reducing agents that disrupt or rearrange the disulfide bonds of the inhibitors. Suitable reducing agents include sodium sulfite, cysteine, N-acetylcysteine, any other conventional reducing agent, and combinations thereof.

The addition of such reducing agents may be effected at various stages of the overall process. The reducing agent may be added with the non-soy oilseed protein source material in the extraction step, may be added to the aqueous non-soy oilseed protein solution following removal of residual non-soy oilseed protein source material, may be added to the diafiltered retentate before drying or may be dry blended with the dried non-soy oilseed protein product. The addition of the reducing agent may be combined with the heat treatment step and membrane processing steps, as described above.

If it is desired to retain active trypsin inhibitors in the protein solution, this can be achieved by eliminating or reducing the intensity of the heat treatment step, not utilizing reducing agents, operating the optional concentration and optional diafiltration steps at the higher end of the pH range, such as 2.5 to 4.0, utilizing a concentration and diafiltration membrane with a smaller pore size, operating the membrane at lower temperatures and employing fewer volumes of diafiltration medium.

The optionally concentrated and optionally diafiltered protein solution may be subject to a further defatting operation, if required. Defatting of the optionally concentrated and optionally diafiltered protein solution may be achieved by any conventional procedure.

The optionally concentrated and optionally diafiltered acidified aqueous protein solution may be treated with an adsorbent, such as granulated activated carbon, to remove colour and/or odour compounds. Such adsorbent treatment may be carried out under any conventional conditions, generally at the ambient temperature of the protein solution.

The optionally concentrated and optionally diafiltered aqueous non-soy oilseed protein solution may be pasteurized prior to drying or further processing. Such pasteurization may be effected under any conventional pasteurization conditions. Generally, the optionally concentrated and optionally diafiltered non-soy oilseed protein solution is heated to a temperature of about 55° to about 85° C. for about 10 seconds to about 60 minutes, preferably about 60° C. to about 70° C. for about 10 minutes to about 60 minutes or about 70° C. to about 85° C. for about 10 seconds to about 60 seconds. The pasteurized non-soy oilseed protein solution then may be cooled, such as to a temperature of about 20° to about 35° C.

The optionally concentrated, optionally diafiltered and optionally pasteurized non-soy oilseed protein solution then may be dried by any conventional means such as spray drying or freeze drying to provide a non-soy oilseed protein product. Alternatively, the optionally concentrated, optionally diafiltered and optionally pasteurized non-soy oilseed protein solution may be raised in pH to a value of less than about 8.0, preferably about 6.0 to about 8.0, more preferably about 6.5 to about 7.5 prior to optional drying. The pH may be raised in any conventional manner such as by the addition of sodium hydroxide, potassium hydroxide or any other conventional food grade alkali solution and combinations thereof. If the protein solution is not pasteurized before pH adjustment, the pasteurization may be conducted after the pH adjustment using the conditions described above.

The non-soy oilseed protein product (prepared with or without the pH adjustment step prior to optional drying) has a protein content greater than about 60 wt % d.b. Preferably, the non-soy oilseed protein product is an isolate with a protein content in excess of about 90 wt % protein (N×6.25) d.b.

In accordance with another aspect of the present invention, the acid insoluble solid material captured after adjustment of the pH of the non-soy oilseed protein solution to the range of about 1.5 to a value about 1 unit below the typical pH of isoelectric precipitation, preferably about 2.0 to about 2.5 may be optionally diluted with RO water then optionally dried to form a non-soy oilseed protein product having a protein content of at least about 60 wt % (N×6.25) d.b. Alternatively, the pH of the optionally diluted acid insoluble solid material may be raised to a value less than about 8.0, preferably about 6.0 to about 8.0, more preferably about 6.5 to about 7.5 by any conventional means such as by the addition of sodium hydroxide solution, potassium hydroxide or any other conventional food grade alkali solution and combinations thereof prior to optional drying to form a non-soy oilseed protein product having a protein content of at least about 60 wt % (N×6.25) d.b.

Preferably, the acid insoluble solid material is washed in order to remove contaminants and improve the purity and flavour of the product. The acid insoluble solid material may be washed by suspending the solids in between about 1 and about 20 volumes, preferably about 1 to about 10 volumes of RO water containing food grade acid to adjust the water to a pH within the range of about 1.5 to a value about 1 unit below the typical pH of isoelectric precipitation and preferably matching the pH of the acid insoluble solid material. The washing step may be conducted at any conventional temperature such as about 15° to about 35° C. The acid insoluble solid material is mixed with the wash solution for any conventional length of time, preferably 15 minutes or less. The washed acid insoluble solid material may then be separated from the wash water by any conventional means such as by centrifugation using a disc stack centrifuge. The wash water may be added to the acidified protein solution for further processing as discussed above. The washed acid insoluble solid material may be optionally diluted with RO water then optionally dried by any conventional means such as spray drying or freeze drying to provide a non-soy oilseed protein product having a protein content of at least about 60 wt % (N×6.25) d.b. Alternatively, the pH of the optionally diluted washed acid insoluble solid material may be raised to a value of less than about 8.0, preferably about 6.0 to about 8.0, more preferably about 6.5 to about 7.5 by any conventional means such as by the addition of sodium hydroxide solution, potassium hydroxide solution or any other conventional food grade alkali solution and combinations thereof, prior to optional drying.

As a further alternative, the acid insoluble solid material may be simultaneously washed and adjusted in pH. The acid insoluble solid material may be initially suspended in between about 1 and about 20 volumes, preferably about 1 to about 10 volumes of RO water and then the pH of the suspended solids raised to a value of less than about 8.0, preferably about 5.0 to about 8.0, by any conventional means such as by the addition of sodium hydroxide solution, potassium hydroxide solution or any other conventional food grade alkali solution and combinations thereof. The acid insoluble solid material is mixed with the wash solution for any conventional length of time, preferably 15 minutes or less. The simultaneously washed and pH adjusted solid material may then be separated from the wash solution by any conventional means such as by centrifugation using a disc stack centrifuge. The wash solution may be discarded or further processed by any conventional means to recover additional protein. The simultaneously washed and pH adjusted acid insoluble solid material may be optionally diluted with RO water then optionally dried by any conventional means such as spray drying or freeze drying to provide a non-soy oilseed protein product having a protein content of at least about 60 wt % (N×6.25) d.b. Alternatively, the simultaneously washed and pH adjusted acid insoluble solid material may be optionally diluted with RO water then further raised in pH as to a value less than about 8.0, preferably between about 6.0 and about 8.0 and more preferably between about 6.5 and about 7.5 and then optionally dried.

The flavour of products derived from the acid insoluble solid material may be generally higher in beany, green, vegetable or similar notes compared to the products prepared by processing the acid soluble protein fraction. However, the flavour of the products derived from the acid insoluble solid material is such that the products are suitable for use in food and beverage applications.

A pasteurization step may be employed on the optionally diluted acid insoluble solid material or optionally diluted washed acid insoluble solid material or optionally diluted washed and pH adjusted acid insoluble solid material prior to the optional drying step. Such pasteurization may be effected under any conventional pasteurization conditions. Generally, the optionally diluted acid insoluble solid material or optionally diluted washed acid insoluble solid material or optionally diluted washed and pH adjusted acid insoluble solid material is heated to a temperature of about 55° to about 85° C. for about 10 seconds to about 60 minutes, preferably about 60° C. to about 70° C. for about 10 minutes to about 60 minutes or about 70° C. to about 85° C. for about 10 seconds to about 60 seconds. The pasteurized optionally diluted acid insoluble solid material or optionally diluted washed acid insoluble solid material or optionally diluted washed and pH adjusted acid insoluble solid material then may be cooled, such as to a temperature of about 20° to about 35° C. If the optionally diluted acid insoluble solid material or optionally diluted washed acid insoluble solid material is not pasteurized before pH adjustment, the pasteurization may be conducted after the pH adjustment using the conditions described above. Optionally the simultaneously washed and pH adjusted acid insoluble solid material may be pasteurized after the further pH adjustment step described above.

DESCRIPTION OF AN ASPECT OF THE INVENTION

Referring now to FIG. 1, which shows a process 10 according to one aspect of the present invention, a non-soy oilseed protein source is subjected to an initial extraction with water, at a pH of about 6 to about 11, preferably about 7.0 to about 8.5 at 12. The protein extract solution then is completely or partially clarified by the removal of residual non-soy oilseed protein source at 14, with the removed solids being collected at 16. The protein extract solution 18 then is adjusted in pH at 20 to about 1.5 to a value about 1 unit below the typical pH of isoelectric precipitation, preferably about 2.0 to about 2.5. The acid insoluble material is removed by centrifugation at 22 yielding acid insoluble solid material at 24 and an acidified protein solution at 26.

The recovered acid insoluble solid material may be optionally washed at 28 with water having the same pH as the solids, namely about 1.5 to a value about 1 unit below the typical pH of isoelectric precipitation, preferably about 2.0 to about 2.5, and the optionally washed solids 34 may be optionally adjusted in pH to a value less than about 6.0 at 46 then dried at 48 to provide a soy protein product designated *810PA at 50 having a protein content of at least about 60 wt % (N×6.25) d.b.

Alternatively, the optionally washed solids 34 are adjusted to a pH of generally about 6.0 to about 8.0, preferably about 6.5 to about 7.5, at 36 and dried at 38, to provide a soy protein product designated *810PN at 40 having a protein content of at least about 60 wt % (N×6.25) d.b.

The wash centrate 30 from the optional washing step 28 may be added to the acidified protein solution 26. The solution of soluble protein may be filtered at 32. The solution of soluble protein may be lowered in pH within the range of about 1.5 to a value about 1 unit below the typical pH of isoelectric precipitation, preferably about 2.0 to about 2.5 at 60. The solution of soluble protein is then subjected to optional concentration and/or optional diafiltration at 62. The retentate 64 from the optional concentration and/or optional diafiltration step may be optionally adjusted in pH to a value less than about 6.0 at 76 then dried at 78 to provide a non-soy oilseed protein product designated *810A at 80, having a protein content of at least about 60 wt % (N×6.25) d.b. Preferably, the *810A product is an isolate having a protein content of at least about 90 wt % (N×6.25) d.b. Alternatively, the retentate 64 from the optional concentration and/or optional diafiltration step is adjusted to a pH of generally about 6.0 to about 8.0, preferably about 6.5 to about 7.5 at 66 then dried at 68 to provide a non-soy oilseed protein product designated *810N at 70, having a protein content of at least about 60 wt % (N×6.25) d.b. Preferably, the *810N product is an isolate having a protein content of at least about 90 wt % (N×6.25) d.b.

The *810A and *810PA protein products may be used on their own or may be combined by dry blending at 84. Alternatively, the combined *810A/*810PA product may be formed by mixing the optionally washed acid insoluble solid material, optionally adjusted to a pH of less than about 6.0 at 46 with the optional concentration/optional diafiltration retentate, optionally adjusted to a pH of less than about 6.0 at 76 and drying the mixture 86. The *810N and *810PN protein products may be used on their own or may be combined by dry blending at 84. Alternatively, the combined *810N/*810PN product may be formed by mixing the optionally washed acid insoluble solid material, adjusted to a pH of about 6.0 to about 8.0, preferably about 6.5 to about 7.5 at 36 with the optional concentration/optional diafiltration retentate, adjusted to a pH of about 6.0 to about 8.0, preferably about 6.5 to about 7.5 at 66 and drying the mixture at 82.

EXAMPLES

Example 1

This Example illustrates the preparation of canola protein products of the present invention.

60 kg of defatted canola meal was added to 600 L of reverse osmosis purified (RO) water along with sufficient NaOH solution to adjust the pH to a target of 7. The mixture was agitated at ambient temperature for 30 minutes to provide an aqueous protein solution. The pH was monitored and maintained at about 7 throughout the extraction time. The bulk of the suspended solids were removed by centrifugation using a decanter centrifuge to provide a protein solution having a protein content of 1.37 wt %. The pH of the partially clarified protein solution was then lowered to about 2.0 by the addition of HCl solution (HCl diluted with an equal volume of water) and the solution centrifuged using a disc stack centrifuge to provide 411 L of acidified protein solution having pH 2.00 and an unrecorded amount of acid insoluble solid material.

410 L of acidified protein solution, having a protein content of 0.59 wt %, was reduced in volume to 50 L by concentration on a polyethersulfone membrane having a molecular weight cutoff of 10,000 daltons, operated at a temperature of about 31° C. The resulting protein solution, with a protein content of 3.48 wt %, was diafiltered on the same membrane with 250 L of RO water at about pH 2, with the diafiltration operation conducted at about 31° C. The diafiltered protein solution, having a protein content of 3.12 wt % was then further concentrated to a protein content of 5.46 wt %. 30.18 kg of diafiltered and concentrated protein solution was obtained and represented a yield of 24.9% of the protein in the post-decanter extract solution. The diafiltered and concentrated protein solution was pasteurized at about 67° C. for 60 seconds. 16.76 kg of pasteurized, diafiltered and concentrated solution, having a pH of 2.17 was spray dried to yield a product found to have a protein content of 80.25% (N×6.25) d.b. The product was termed SD092-D23-15A C810A. 16.20 kg of pasteurized, diafiltered and concentrated protein solution was adjusted to pH 7.45 using NaOH/KOH solution (2.5 kg of 50% w/w NaOH solution mixed with 1.25 kg of KOH flakes and 6.25 kg of water). The pH adjusted, diafiltered and concentrated solution was spray dried to yield a product found to have a protein content of 77.62% (N×6.25) d.b. The product was termed SD092-D23-15A C810N.

The acid insoluble solid material collected had a protein content of 5.11 wt %. A sample of acid insoluble solid material was freeze dried to yield a product found to have a protein content of 75.42% (N×6.25) d.b. The product was termed SD092-D23-15A C810PA.

Example 2

This Example illustrates the preparation of hemp protein products of the present invention.

20 kg of hemp protein powder (51.96% protein as-is) (Hemp Oil Canada, Ste. Agathe, MB) was combined with 200 L of RO water and sufficient NaOH solution to adjust the pH to 8.59 and the mixture agitated for 30 minutes at about 60° C. to provide an aqueous protein solution. The pH was monitored and maintained at about 8.5 throughout the extraction time. The bulk of the suspended solids were removed by centrifugation using a decanter centrifuge to provide a protein solution having a protein content of 2.34 wt %. The partially clarified protein solution was then subjected to a fat removal step by passing the solution through a cream separator. 160 L of the post-separator protein solution was then lowered in pH to 2.09 by the addition of HCl solution (HCl diluted with an equal volume of water) and the solution centrifuged using a disc stack centrifuge to provide 142 L of acidified protein solution having pH 1.99 as well as 19.88 kg of acid insoluble solid material.

132 L of acidified protein solution was reduced in volume to 42 L using a microfiltration system containing ceramic membranes having a pore size of 0.8 µm and operated at a temperature of about 46° C. The sample was then further reduced in volume to 17 L and concurrently diafiltered with 25 L of pH 2 RO water at about 52° C. The microfiltration retentate was then diafiltered with an additional 50 L of pH 2 RO water at about 49° C. The diafiltered retentate had a weight of 16.32 kg and a protein content of 2.05 wt %.

The microfiltration and diafiltration permeates were combined to form a membrane feed solution having a protein content of 1.03 wt % and a pH of 2.04. 190 L of this membrane feed solution was reduced in volume to 33 L using an ultrafiltration system containing a PES membrane having a pore size of 10,000 daltons and operated at a temperature of about 46° C. The protein solution was then diafiltered with 9 volume of pH 2 RO water at about 51° C. followed by one volume of RO water at the natural pH at about 52° C. The diafiltered protein solution was then further concentrated to provide 26.52 kg of protein solution having a protein content of 4.79% and representing a yield of 38.4% of the protein in the post-separator protein solution. The diafiltered and further concentrated protein solution was pasteurized at 72° C. for several minutes. 13.26 kg of the pasteurized protein solution was spray dried to yield a product found to have a protein content of 101.56 wt % (N×6.25) d.b. The product was termed H002-L03-15A H810A. 13.26 kg of the pasteurized protein solution was adjusted to pH 7.15 using a NaOH solution. The pH adjusted solution was diluted with 3.52 L of RO water then spray dried to yield a product found to have a protein content of 98.32 wt % (N×6.25) d.b. The product was termed H002-L03-15A H810N.

The 19.88 kg of acid insoluble solid material was mixed with 40 L of RO water at pH 2 and then the sample centrifuged using a disc stack centrifuge to provide 48 L of acidified wash solution having pH 1.85 as well as 9.34 kg of washed acid insoluble solid material. The acidified wash solution was sampled for analysis and then discarded. 9.34 kg of the washed acid insoluble solid material was pasteurized at 72° C. for several minutes and then the pH adjusted to 7.02 with NaOH solution. This material represented a yield of 10.0% of the protein in the post-separator protein solution. The pH adjusted sample was spray dried to yield a product found to have a protein content of 77.44 wt % (N×6.25) d.b. The product was termed H002-L03-15A H810PN.

The protein content of the hemp products prepared in this Example were found to be higher than the protein content of the commercial hemp protein concentrate Hemp Pro 70 (Manitoba Harvest Hemp Foods, Winnipeg, MB), which was found to have a protein content of 64.98% (N×6.25) d.b.

Example 3

120 g of sunflower meal (33.06% protein as-is) (ADM, Decatur, Ill.) was combined with 1200 ml of RO water and sufficient 6M NaOH solution to adjust the pH to a target of 7.1 and the mixture agitated for 30 minutes at about 60° C. minutes to provide an aqueous protein solution. The pH was monitored and maintained at about 7.1 throughout the extraction time. The bulk of the suspended solids were removed by centrifuging 1271.32 g of extraction slurry at 3,500 g for 3 minutes and then decanting the centrate through a screen. 786.54 g of protein extract solution having a protein content of 1.27 wt % and a pH of 7.31 was collected and cooled to room temperature. 749.31 g of protein extract solution was adjusted in pH to 1.98 by the addition of 6.75 g of HCl solution (HCl diluted with an equal volume of water). 752.01 g of the acidified sample was centrifuged at 7,000 g for 3 minutes and then the centrate decanted to provide 554.89 g of acidified protein solution that was cleanly decanted. Another 169.29 g of acidified protein solution was discarded because it contained a significant amount of acid insoluble solid material (SF810P) that decanted with the centrate.

16.62 g of acid insoluble solid material was collected from the bottom of the centrifuge tube and mixed with 30 ml of RO water. The pH of the sample was then adjusted in pH from 2.29 to 6.92 with 6M NaOH and freeze dried to provide 1.38 g of a product having a protein content of 64.04 wt % on an as-is basis. This product was termed SF810PN.

510.13 g of acidified protein solution, having a protein content of 0.76 wt %, was reduced in volume to about 44 ml using Vivaflow 200 polyethersulfone membranes having a molecular weight cutoff of 10,000 Da. The ultrafiltration retentate was combined with 220 ml of RO water for diafiltration and the pH of the mixture lowered from 2.59 to 2.01 with HCl solution. The sample was then run on the Vivaflow membranes until 222 ml of permeate was collected. The volume of diafiltered, concentrated protein solution was about 44 ml. This sample had a protein content of 5.92 wt % and represented a yield of about 26.0% of the protein in the protein extract solution. 18.33 g of diafiltered and concentrated protein solution was freeze dried as is to provide 1.29 g of product having a protein content of 79.47 wt % on an as-is basis. This product was termed SF810A. A second aliquot of diafiltered and concentrated protein solution was adjusted in pH to 6.94 with NaOH solution and freeze dried to provide 1.34 g of product having a protein content of 77.70 wt % on an as-is basis. This product was termed SF810N.

Example 4

This Example contains an evaluation of the dry colour of the hemp protein products prepared according to Example 2 compared to that of the commercial hemp protein concentrate Hemp Pro 70 (Manitoba Harvest Hemp Foods, Winnipeg, MB). Dry colour was assessed using a HunterLab ColorQuest XE operated in reflectance mode. The results are shown in the following Table 1.

TABLE 1

| Dry colour of protein products | | | |
|---|---|---|---|
| Product | L* | a* | b* |
| H002-L03-15A H810A | 76.24 | 0.87 | 19.33 |
| H002-L03-15A H810N | 73.64 | 1.08 | 19.48 |
| H002-L03-15A H810PN | 62.14 | 1.44 | 20.19 |
| Hemp Pro 70 | 58.15 | 2.43 | 26.89 |

As may be seen from the results in Table 1, the hemp protein products of the present invention were lighter, less red and less yellow than the commercial hemp protein product evaluated.

Example 5

This Example contains an evaluation of the phytic acid content of the hemp protein products prepared according to the present invention as described in Example 2 and the commercial hemp protein concentrate Hemp Pro 70 (Manitoba Harvest Hemp Foods, Winnipeg, MB). Phytic acid content was determined using the method of Latta and Eskin (J. Agric. Food Chem., 28: 1313-1315).

The results obtained are set forth in the following Table 2.

TABLE 2

Phytic acid content of hemp products

| | % phytic acid |
|---|---|
| H002-L03-15A H810A | 0.56 |
| H002-L03-15A H810N | 0.54 |
| H002-L03-15A H810PN | 2.90 |
| Hemp Pro 70 | 1.95 |

As may be seen from the results in Table 2, the H002-L03-15A H810A and H810N were lower in phytic acid than the commercial hemp protein product.

Example 6

This Example contains an evaluation of the acid hydrolysable carbohydrate content of the hemp protein products prepared according to the present invention as described in Example 2 and the commercial hemp protein concentrate Hemp Pro 70 (Manitoba Harvest Hemp Foods, Winnipeg, MB). The acid hydrolysable carbohydrate content was determined according to the method of Dubois et al. (Anal. Chem., 28: 350-356). The results are shown in the following Table 3.

TABLE 3

Acid hydrolysable carbohydrate content of samples

| sample | % acid hydrolysable carbohydrates d.b. |
|---|---|
| H002-L03-15A H810A | 2.48 |
| H002-L03-15A H810N | 2.70 |
| H002-L03-15A H810PN | 8.07 |
| Hemp Pro 70 | 11.46 |

As may be seen from the results presented in Table 3, the hemp protein products of the present invention, particularly the H810A and H810N, were lower in acid hydrolysable carbohydrate than the commercial hemp protein product.

Example 7

This Example illustrates a comparison of the flavour of H002-L03-15A H810N, prepared as described in Example 2 with that of the commercial hemp protein concentrate Hemp Pro 70 (Manitoba Harvest Hemp Foods, Winnipeg, MB).

Samples were prepared for sensory evaluation by dissolving sufficient protein powder to supply 3 g of protein in 150 ml purified drinking water. The pH of the solution of H810N was determined to be 6.00 while the pH of the solution of Hemp Pro 70 was 7.48. Food grade NaOH was added to the solution of H810N to raise the pH to 7.48. An informal panel of ten panelists was asked to blindly compare the samples and indicate which had a cleaner flavour.

Nine out of ten panelists indicated that the flavour of the H810N was cleaner. One panelist indicated that the flavour of the Hemp Pro 70 was cleaner.

Example 8

This Example illustrates a comparison of the flavour of H002-L03-15A H810PN, prepared as described in Example 2 with that of the commercial hemp protein concentrate Hemp Pro 70 (Manitoba Harvest Hemp Foods, Winnipeg, MB).

Samples were prepared for sensory evaluation by dissolving sufficient protein powder to supply 2 g of protein in 100 ml purified drinking water. The pH of the solution of H810PN was determined to be 7.13 while the pH of the solution of Hemp Pro 70 was 7.51. Food grade NaOH was added to the solution of H810PN to raise the pH to 7.51. An informal panel of seven panelists was asked to blindly compare the samples and indicate which had a cleaner flavour.

Four out of seven panelists indicated that the flavour of the H810N was cleaner. Three panelists indicated that the flavour of the Hemp Pro 70 was cleaner.

Example 9

This Example illustrates the protein solubility of the hemp protein products prepared according to the present invention as described in Examples 2. Protein solubility was tested by a modified version of the procedure of Mon et al., J. Food Sci., 50: 1715-1718.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with diluted NaOH or HCl. The pH was measured and corrected periodically during the 60 minutes stirring. After the 60 minutes of stirring, the samples were made up to 50 ml total volume with RO water, yielding a 1% w/v protein dispersion. The protein content of the dispersions was measured by combustion analysis using a Leco Nitrogen Determinator. Aliquots of the dispersions were then centrifuged at 7,800 g for 10 minutes, which sedimented insoluble material and yielded a supernatant. The protein content of the supernatant was measured by Leco analysis and the solubility of the product calculated as follows:

Protein solubility (%)=(% protein in supernatant/% protein in initial dispersion)×100 Values calculated as greater than 100% were reported as 100%.

The protein solubility of the products at different pH values is shown in Table 4.

TABLE 4

Protein solubility of hemp protein products at different pH values

| | Solubility (%) | | | | | |
|---|---|---|---|---|---|---|
| sample | pH 2 | pH 3 | pH 4 | pH 5 | pH 6 | pH 7 |
| H002-L03-15A H810A | 100 | 99.0 | 100 | 15.4 | 15.3 | 12.8 |
| H002-L03-15A H810N | 52.0 | 36.7 | 24.0 | 17.4 | 12.8 | 13.5 |

As may be seen from the results presented in Table 4, the H810A product was highly soluble in the pH range 2-4.

Example 10

This Example further illustrates preparation of hemp protein products according to the present invention.

'a' kg of 'b' was combined with 'c' L of RO water and sufficient 12.5% NaOH/12.5% KOH solution to adjust the pH to a target of 'd' and the mixture agitated for 30 minutes at about 60° C. to provide an aqueous protein solution. The pH was monitored and maintained at about 'd' throughout the extraction time. The bulk of the suspended solids were removed by centrifugation using a decanter centrifuge to provide a protein solution having a protein content of 'e' wt %. The protein solution was then lowered in pH to a target of 2 by the addition of HCl solution (HCl diluted with an equal volume of water) and the solution centrifuged using a disc stack centrifuge to provide 'f' L of acidified protein solution having pH of 'g' and a protein content of 'h' wt % as well as 'i' kg of acid insoluble solid material having a protein content of T wt %. The acidified protein solution was 'k'.

'l' L of 'm' acidified protein solution having a protein content of 'n' wt % was reduced in volume to 'o' L using an ultrafiltration system containing a PES membrane having a pore size of 10,000 daltons and operated at a temperature of about 'r' ° C. The protein solution, having a protein content of 'q' wt % was then diafiltered with 'r' L of RO water adjusted to pH 2 at about 's'° C., followed by 't' L of RO water at the natural pH at about 'u'° C. The diafiltered protein solution had a protein content of 'v' wt %. This solution was further concentrated to 'w' wt % protein then pasteurized at 'x'° C. for 'y' seconds. 'z' kg of the pasteurized protein solution was spray dried to yield a product found to have a protein content of aa' wt % (N×6.25) d.b. The product was termed 'ab' H810A. 'ac' kg of the pasteurized protein solution was adjusted to pH 'ad' using a 12.5% NaOH/12.5% KOH solution. The pH adjusted solution was spray dried to yield a product found to have a protein content of 'ae' wt % (N×6.25) d.b. The product was termed 'ab' H810N.

'af' kg of acid insoluble material was combined with 'ag' L of RO water and the pH adjusted to 'A' with 12.5% NaOH/12.5% KOH solution. The sample was then centrifuged again to provide 'ai' kg of washed acid insoluble solids having a protein content of 'aj'. These solids were pasteurized at 'ak'° C. for 'al' and then spray dried to yield a product found to have a protein content of 'am' wt % (N×6.25) d.b. The product was termed 'ab' H810PA.

The parameters 'a' to 'am' are set forth in the following Table 5.

TABLE 5

Parameters for the runs to produce hemp protein products

| | | | | |
|---|---|---|---|---|
| aa | H003-I15-16A | H003-I27-16A | H005-K01-16A | H003-L05-16A |
| a | 24 | 30 | 29 | 60 |
| b | hull material from the dehulling of hemp seeds, defatted by pressing then ground | hull material from the dehulling of hemp seeds, defatted by pressing then ground | "seed meats" (unders) obtained by sieving hull material from the dehulling of hemp seeds, defatted by pressing then ground | hull material from the dehulling of hemp seeds, defatted by pressing then ground |
| c | 240 | 300 | 290 | 600 |
| d | 8.5 | 10.5 | 8.5 | 8.5 |
| e | 0.66 | 1.20 | 2.05 | 0.96 |
| f | 220 | 225 | 212 | 508 |
| g | 1.80 | 1.96 | 2.12 | 2.00 |
| h | 0.58 | 1.20 | 1.83 | 0.88 |
| i | 23.86 | 50.70 | 52.2 | 73.74 |
| j | 0.93 | 1.43 | not recorded | 1.21 |
| k | further clarified | further clarified | N/A | further clarified |

TABLE 5-continued

Parameters for the runs to produce hemp protein products

| | by successive filtration through filter pads having pore sizes of 2.0 μm and 0.8 μm | by successive filtration through filter pads having pore sizes of 2.0 μm and 0.2 μm | | by successive filtration through filter pads having pore sizes of 2.0 μm and 0.2 μm |
|---|---|---|---|---|
| l | 245 | 250 | 212 | 462 |
| m | filtered | filtered | N/A | filtered |
| n | 0.49 | 0.90 | 1.83 | 0.58 |
| o | 25 | 31 | 65 | 46 |
| p | 48 | 46 | 51 | 45 |
| q | 3.06 | 5.52 | 5.10 | 5.59 |
| r | 225 | 279 | 585 | 414 |
| s | 52 | 50 | 52 | 50 |
| t | 215 | 31 | 94 | 141 |
| u | 52 | 50 | 52 | 51 |
| v | 3.70 | 5.27 | 5.70 | 3.30 |
| w | N/A | 6.92 | 10.26 | 5.64 |
| x | 72 | 74 | 76 | about 72 |
| y | not recorded, about 30 to 60 | 16 | 16 | 16 |
| z | 11.80 | 14.05 | N/A | N/A |
| aa | 98.95 | 99.45 | N/A | N/A |
| ac | 11.34 | 14.69 | 32.66 | 39.62 |
| ad | 7.45 | 6.95 | 6.80 | 7.06 |
| ae | 95.75 | 95.58 | 75.20 | 95.61 |
| af | N/A | 50.70 | 52.20 | 73.74 |
| ag | N/A | 202 | 210 | 295 |
| ah | N/A | about 5.5 | about 5.5 | 5.63 |
| ai | N/A | 18.98 | 23.18 | 28.56 |
| aj | N/A | 3.74 | 4.52 | 1.97 |
| ak | N/A | 74 | 74 | about 72 |
| al | N/A | 16 | 16 | 16 |
| am | N/A | 79.30 | 78.14 | 68.86 |

Example 11

This Example further illustrates preparation of hemp protein products according to the present invention.

30 kg of hull material from the dehulling of hemp seeds, defatted by pressing then ground was combined with 300 L of RO water and sufficient 12.5% NaOH/12.5% KOH solution to adjust the pH to a target of 8.5 and the mixture agitated for 30 minutes at about 60° C. to provide an aqueous protein solution. The pH was monitored and maintained at about 8.5 throughout the extraction time. The bulk of the suspended solids were removed by centrifugation using a decanter centrifuge to provide a protein solution having a protein content of 0.95 wt %. The protein solution was then lowered in pH to a target of 2 by the addition of HCl solution (HCl diluted with an equal volume of water). 42.62 kg of wet solids from the initial separation step were combined with 300 L of RO water and mixed for 30 minutes at 60° C. The pH of the suspension was 8.79 so no further pH adjustment was conducted. Again the suspended solids were removed by centrifugation using a decanter centrifuge to provide a protein solution having a protein content of 0.16 wt %. The pH of this solution was lowered to about 2 and the two acidified protein solutions were combined and centrifuged using a disc stack centrifuge to provide 598 L of acidified protein solution having pH of 1.92 and a protein content of 0.48 wt % as well as an unrecorded amount of acid insoluble solid material having a protein content of 0.80 wt %.

The acidified protein solution was further clarified by successive filtration through filter pads having pore sizes of 2.0 μm and 0.2 μm.

585 L of filtered acidified protein solution having a protein content of 0.33 wt % was reduced in volume to 40 L using an ultrafiltration system containing a PES membrane having a pore size of 10,000 daltons and operated at a temperature of about 45° C. The protein solution, having a protein content of 4.90 wt % was then diafiltered with 360 L of RO water adjusted to about pH 2 at about 51° C., followed by an unrecorded amount of RO water at the natural pH at about 50° C. The diafiltered protein solution had a protein content of 4.30 wt %. This solution was further concentrated to 4.43 wt % protein then pasteurized at 75° C. for 16 seconds. 30.36 kg of the pasteurized protein solution was adjusted to pH 6.74 using a 12.5% NaOH/12.5% KOH solution. The pH adjusted solution was spray dried to yield a product found to have a protein content of 93.48% (N×6.25) d.b. The product was termed H003-K24-16A H810N.

Example 12

This Example contains an evaluation of the dry colour of the hemp protein products prepared according to Examples 10 and 11. Dry colour was assessed using a HunterLab ColorQuest XE operated in reflectance mode. The results are shown in the following Table 6.

TABLE 6

Dry colour of protein products

| Product | L* | a* | b* |
|---|---|---|---|
| H003-I15-16A H810A | 75.29 | 1.20 | 18.23 |
| H003-I27-16A H810A | 66.77 | 5.44 | 20.26 |
| H003-I15-16A H810N | 70.78 | 1.59 | 19.69 |
| H003-I27-16A H810N | 61.34 | 6.17 | 18.94 |
| H005-K01-16A H810N | 67.03 | 0.22 | 27.13 |
| H003-K24-16A H810N | 67.49 | 1.75 | 19.82 |
| H003-L05-16A H810N | 71.21 | 0.61 | 17.01 |
| H003-I27-16A H810PA | 52.12 | 3.57 | 14.48 |
| H005-K01-16A H810PA | 67.33 | 0.44 | 21.05 |
| H003-L05-16A H810PA | 65.62 | 1.19 | 19.53 |

As may be seen from the results in Table 6, with the exception of the H810PA from the pH 10.5 extraction run, the hemp protein products of the present invention were lighter than the commercial hemp protein product evaluated (see Table 1).

Example 13

This Example contains an evaluation of the phytic acid content of the hemp protein products prepared according to the present invention as described in Examples 10 and 11. Phytic acid content was determined using the method of Latta and Eskin (J. Agric. Food Chem., 28: 1313-1315).

The results obtained are set forth in the following Table 7.

TABLE 7

Phytic acid content of hemp products

| sample | % phytic acid |
|---|---|
| H003-I15-16A H810A | 0.00 |
| H003-I27-16A H810A | 0.08 |
| H003-I15-16A H810N | 0.12 |
| H003-I27-16A H810N | 0.09 |
| H005-K01-16A H810N | 1.05 |
| H003-K24-16A H810N | 0.02 |
| H003-L05-16A H810N | 0.05 |

TABLE 7-continued

Phytic acid content of hemp products

| sample | % phytic acid |
|---|---|
| H003-I27-16A H810PA | 0.40 |
| H005-K01-16A H810PA | 0.75 |
| H003-L05-16A H810PA | 0.85 |

As may be seen from the results in Table 7, the hemp protein products were all generally low in phytic acid and were lower in phytic acid than the commercial hemp protein product (see Table 2).

Example 14

This Example contains an evaluation of the acid hydrolysable carbohydrate content of the hemp protein products prepared according to the present invention as described in Examples 10 and 11. The acid hydrolysable carbohydrate content was determined according to the method of Dubois et al. (Anal. Chem., 28: 350-356). The results are shown in the following Table 8.

TABLE 8

Acid hydrolysable carbohydrate content of samples

| sample | % acid hydrolysable carbohydrates d.b. |
|---|---|
| H003-I15-16A H810A | 3.26 |
| H003-I27-16A H810A | 3.61 |
| H003-I15-16A H810N | 3.44 |
| H003-I27-16A H810N | 3.40 |
| H003-K24-16A H810N | 2.75 |
| H003-L05-16A H810N | 3.70 |
| H003-I27-16A H810PA | 5.64 |
| H003-L05-16A H810PA | 6.76 |

As may be seen from the results presented in Table 8, the hemp protein products of the present invention, particularly the H810A and H810N, were lower in acid hydrolysable carbohydrate than the commercial hemp protein product (see Table 3).

Example 15

This Example illustrates the protein solubility of the hemp protein products prepared according to the present invention as described in Examples 2, 10 and 11 and the commercial hemp protein concentrate Hemp Pro 70 (Manitoba Harvest Hemp Foods, Winnipeg, MB). Protein solubility was tested by a modified version of the procedure of Mon et al., J. Food Sci., 50: 1715-1718.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with diluted NaOH or HCl. The pH was measured and corrected periodically during the 60 minutes stirring. After the 60 minutes of stirring, the samples were made up to 50 ml total volume with RO water, yielding a 1% w/v protein dispersion. The protein content of the dispersions was measured by combustion analysis using a Leco Nitrogen Determinator. Aliquots of the dispersions were then centrifuged at 7,800 g for 10 minutes, which sedimented insoluble material and yielded a supernatant. The protein content of the supernatant was measured by Leco analysis and the solubility of the product calculated as follows:

Protein solubility (%)=(% protein in supernatant/% protein in initial dispersion)×100 Values calculated as greater than 100% were reported as 100%.

The protein solubility of the products at different pH values is shown in Table 9.

TABLE 9

Protein solubility of hemp protein products at different pH values

| | Solubility (%) | | | | | |
|---|---|---|---|---|---|---|
| sample | pH 2 | pH 3 | pH 4 | pH 5 | pH 6 | pH 7 |
| H003-I15-16A H810A | 99.0 | 83.0 | 89.8 | 66 | 15.7 | 21.0 |
| H003-I27-16A H810A | 99.1 | 97.2 | 97.1 | 16.2 | 8.6 | 11.5 |
| H003-I27-16A H810N | 100 | 100 | 52.4 | 18.1 | 12.5 | 15.6 |
| H005-K01-16A H810N | 38.2 | 31.9 | 13.7 | 0.0 | 5.3 | 7.1 |
| H003-L05-16A H810N | 34.0 | 28.8 | 17.3 | 7.9 | 4.7 | 13.4 |
| H005-K01-16A H810PA | 14.4 | 0.0 | 5.8 | 0.0 | 1.0 | 0.9 |
| H003-L05-16A H810PA | 21.2 | 0.0 | 0.0 | 0.0 | 0.0 | 4.3 |
| H002-L03-15A H810PN | 10.0 | 9.3 | 5 | 1.9 | 6.8 | 13.9 |
| Hemp Pro 70 | 52.5 | 53.1 | 16.8 | 15.1 | 13.4 | 21.9 |

As may be seen from the results in Table 9, the H810A had good protein solubility in the pH range 2 to 4. The protein solubility of the H810N was low in the pH range 5 to 7. The products derived from the acid insoluble solid material were generally low in protein solubility across the pH range tested.

Example 16

This Example illustrates the molecular weight profile of the hemp protein products prepared according to aspects of the present invention as described in Examples 2, 10 and 11 as well as hemp protein product prepared as described in U.S. patent application Ser. No. 13/956,619 (US Patent Publication No. 2014/0037824 published Feb. 6, 2014) and the commercial hemp protein product Hemp Pro 70 (Manitoba Harvest Hemp Foods, Winnipeg, MB).

Molecular weight profiles were determined by size exclusion chromatography using a Varian ProStar HPLC system equipped with a 300×7.8 mm Phenomenex Yarra SEC-2000 series column. The column contained hydrophilic bonded silica rigid support media, 3 micron diameter, with 145 Angstrom pore size.

Before the pulse protein samples were analyzed, a standard curve was prepared using a Biorad protein standard (Biorad product #151-1901) containing proteins with known molecular weights between 17,000 Daltons (myoglobulin) and 670,000 Daltons (thyroglobulin) with Vitamin B12 added as a low molecular weight marker at 1,350 Daltons. A 0.9% w/v solution of the protein standard was prepared in water, filtered with a 0.45 µm pore size filter disc then a 50 µL aliquot run on the column using a mobile phase of 0.05M phosphate/0.15M NaCl, pH 6 containing 0.02% sodium azide. The mobile phase flow rate was 1 mL/min and components were detected based on absorbance at 280 nm. Based on the retention times of these molecules of known molecular weight, a regression formula was developed relating the log of the molecular weight to the retention time in minutes.

For the analysis of the pulse protein samples, 0.05M phosphate/0.15M NaCl, pH 6 containing 0.02% sodium azide was used as the mobile phase and also to dissolve dry samples. Protein samples were mixed with mobile phase solution to a concentration of 1% w/v, placed on a shaker for at least 1 hour then filtered using 0.45 µm pore size filter discs. Sample injection size was 50 µL. The mobile phase flow rate was 1 mL/minute and components were detected based on absorbance at 280 nm.

The regression formula relating molecular weight and retention time was used to calculate retention times that corresponded to molecular weights of 100,000 Da, 15,000 Da, 5,000 Da and 1,000 Da. The HPLC ProStar system was used to calculate the peak areas lying within these retention time ranges and the percentage of protein ((range peak area/total protein peak area)×100) falling in a given molecular weight range was calculated. Note that the data was not corrected by protein response factor.

The molecular weight profiles of the hemp protein products are shown in Table 10.

TABLE 10

HPLC protein profile of various products

| product | % > 100,000 Da | % 15,000-100,000 Da | % 5,000-15,000 Da | % 1,000-5,000 Da |
|---|---|---|---|---|
| H002-L03-15A H810A | 1.3 | 19.0 | 48.9 | 30.8 |
| H003-I15-16A H810A | 3.6 | 23.1 | 46.3 | 27.0 |
| H003-I27-16A H810A | 2.6 | 21.7 | 46.6 | 29.1 |
| H002-L03-15A H810N | 1.3 | 21.3 | 43.6 | 33.7 |
| H003-I15-16A H810N | 3.3 | 28.3 | 45.0 | 23.4 |
| H003-I27-16A H810N | 2.3 | 29.1 | 43.7 | 24.9 |
| H005-K01-16A H810N | 0.5 | 22.4 | 44.0 | 33.1 |
| H003-K24-16A H810N | 2.5 | 24.8 | 43.1 | 29.7 |
| H003-L05-16A H810N | 4.3 | 25.5 | 45.0 | 25.2 |
| H003-I27-16A H810PA | 11.6 | 61.2 | 13.4 | 13.8 |
| H005-K01-16A H810PA | 2.3 | 52.3 | 30.2 | 15.2 |
| H003-L05-16A H810PA | 0.0 | 34.0 | 40.9 | 25.0 |
| H002-L03-15A H810PN | 0.5 | 38.2 | 40.8 | 20.4 |
| H001-H24-11A H701 | 0.3 | 15.6 | 63.6 | 20.5 |
| Hemp Pro 70 | 1.7 | 12.8 | 15.8 | 69.7 |

As may be seen from the results of Table 10, the protein profiles of the products of the present invention differed from the profiles of the H701 and the commercial hemp protein concentrate.

Example 17

This Example illustrates a comparison of the flavour of H003-I15-16A H810N, prepared as described in Example 10 with that of the commercial hemp protein concentrate Hemp Pro 70 (Manitoba Harvest Hemp Foods, Winnipeg, MB).

Samples were prepared for sensory evaluation by dissolving sufficient protein powder to supply 2.4 g of protein in 120 ml purified drinking water. The pH of the solution of H810N was determined to be 6.86 while the pH of the solution of Hemp Pro 70 was 7.71. Food grade HCl was added to the solution of Hemp Pro 70 to lower the pH to 6.85. An informal panel of eight panelists was asked to blindly compare the samples and indicate which had a cleaner flavour.

Eight out of eight panelists indicated that the flavour of the H810N was cleaner.

Example 18

This Example illustrates a comparison of the flavour of H005-K01-16A H810N, prepared as described in Example 10 with that of the commercial hemp protein concentrate Hemp Pro 70 (Manitoba Harvest Hemp Foods, Winnipeg, MB).

Samples were prepared for sensory evaluation by dissolving sufficient protein powder to supply 2.4 g of protein in 120 ml purified drinking water. The pH of the solution of H810N was determined to be 6.71 while the pH of the solution of Hemp Pro 70 was 7.74. Food grade HCl was added to the solution of Hemp Pro 70 to lower the pH to 6.67. An informal panel of nine panelists was asked to blindly compare the samples and indicate which had a cleaner flavour.

Seven out of nine panelists indicated that the flavour of the H810N was cleaner. One panelist indicated that the flavour of the Hemp Pro 70 was cleaner, while one panelist could not identify one sample as having a cleaner flavour.

Example 19

This Example illustrates a comparison of the flavour of H003-K24-16A H810N, prepared as described in Example 11 with that of the commercial hemp protein concentrate Hemp Pro 70 (Manitoba Harvest Hemp Foods, Winnipeg, MB).

Samples were prepared for sensory evaluation by dissolving sufficient protein powder to supply 2.4 g of protein in 120 ml purified drinking water. The pH of the solution of H810N was determined to be 6.71 while the pH of the solution of Hemp Pro 70 was 7.74. Food grade HCl was added to the solution of Hemp Pro 70 to lower the pH to 6.67. An informal panel of eight panelists was asked to blindly compare the samples and indicate which had a cleaner flavour.

Six out of eight panelists indicated that the flavour of the H810N was cleaner. Two panelists could not identify one sample as having a cleaner flavour.

Example 20

This Example illustrates a comparison of the flavour of H002-L03-15A H810A, prepared as described in Example 2 with that of the commercial hemp protein concentrate Hemp Pro 70 (Manitoba Harvest Hemp Foods, Winnipeg, MB).

Samples were prepared for sensory evaluation by dissolving sufficient protein powder to supply 2.4 g of protein in 120 ml purified drinking water. The pH of the solution of H810A was determined to be 3.01 while the pH of the solution of Hemp Pro 70 was 7.89. Food grade HCl was added to the solution of Hemp Pro 70 to lower the pH to 3.06. An informal panel of nine panelists was asked to blindly compare the samples and indicate which had a cleaner flavour.

Eight out of nine panelists indicated that the flavour of the H810A was cleaner. One panelist could not identify one sample as having cleaner flavour.

Example 21

This Example illustrates a comparison of the flavour of H003-I15-16A H810A, prepared as described in Example 10 with that of the commercial hemp protein concentrate Hemp Pro 70 (Manitoba Harvest Hemp Foods, Winnipeg, MB).

Samples were prepared for sensory evaluation by dissolving sufficient protein powder to supply 2.4 g of protein in 120 ml purified drinking water. The pH of the solution of H810A was determined to be 3.89 while the pH of the solution of Hemp Pro 70 was 7.68. Food grade HCl was added to the solution of Hemp Pro 70 to lower the pH to 3.89. An informal panel of nine panelists was asked to blindly compare the samples and indicate which had a cleaner flavour.

Eight out of nine panelists indicated that the flavour of the H810A was cleaner. One panelist could not identify one sample as having cleaner flavour.

Example 22

This Example illustrates a comparison of the flavour of H005-K01-16A H810PA, prepared as described in Example 10 with that of the commercial hemp protein concentrate Hemp Pro 70 (Manitoba Harvest Hemp Foods, Winnipeg, MB).

Samples were prepared for sensory evaluation by dissolving sufficient protein powder to supply 2.4 g of protein in 120 ml purified drinking water. The pH of the solution of H810PA was determined to be 6.14 while the pH of the solution of Hemp Pro 70 was 7.72. Food grade HCl was added to the solution of Hemp Pro 70 to lower the pH to 6.17. An informal panel of nine panelists was asked to blindly compare the samples and indicate which had a cleaner flavour.

Six out of nine panelists indicated that the flavour of the H810PA was cleaner. Two panelists indicated that the flavour of the Hemp Pro 70 was cleaner and one panelist could not identify one sample as having cleaner flavour.

Example 23

This Example illustrates a comparison of the flavour of H005-L05-16A H810PA, prepared as described in Example 10 with that of the commercial hemp protein concentrate Hemp Pro 70 (Manitoba Harvest Hemp Foods, Winnipeg, MB).

Samples were prepared for sensory evaluation by dissolving sufficient protein powder to supply 2.4 g of protein in 120 ml purified drinking water. The pH of the solution of H810PA was determined to be 5.88 while the pH of the solution of Hemp Pro 70 was 7.71. Food grade HCl was added to the solution of Hemp Pro 70 to lower the pH to 5.86. An informal panel of nine panelists was asked to blindly compare the samples and indicate which had a cleaner flavour.

Seven out of nine panelists indicated that the flavour of the H810PA was cleaner. Two panelists indicated that the flavour of the Hemp Pro 70 was cleaner.

SUMMARY OF THE DISCLOSURE

In summary of this disclosure, there are provided novel and inventive non-soy oilseed protein products of enhanced taste and novel and inventive methods of producing non-soy oilseed protein products of enhanced taste, which methods do not involve the direct addition and use of calcium salts or other salts for extraction of the non-soy oilseed protein from the non-soy oilseed protein source or in any other process step. Modifications are possible within the scope of this invention.

What we claim is:

1. A process of producing a non-soy oilseed protein product having a protein content of at least about 60 wt % (N×6.25) on a dry weight basis, which process comprises:
(a) extracting a non-soy oilseed protein source with water to cause solubilization of protein from the protein source and to form an aqueous protein solution, (b) at least partially separating the aqueous non-soy oilseed protein solution from residual non-soy oilseed protein source, (c) adjusting the pH of the aqueous non-soy oilseed protein solution to a pH of about 1.5 to a value about 1 pH unit lower than the typical pH of isoelectric precipitation to produce an acidified non-soy oilseed protein solution, (d) separating an acid insoluble solid material from the acidified non-soy oilseed protein solution to produce the non-soy oilseed protein solution comprising the non-soy oilseed protein product and the acid insoluble solid material which is a further non-soy oilseed protein product, (e) optionally concentrating the acidified non-soy oilseed protein solution by a selective membrane technique to produce an optionally concentrated non-soy oilseed protein solution, (f) optionally diafiltering the optionally concentrated non-soy oilseed protein solution, to produce an optionally concentrated and optionally diafiltered non-soy oilseed protein solution, and (g) optionally drying the optionally concentrated and optionally diafiltered non-soy oilseed protein solution, wherein the non-soy oilseed protein product is prepared without addition of a salt in any of steps (a) to (g), and wherein the non-soy oilseed protein product and the further non-soy oilseed protein product each have a protein content of at least about 60 wt % (N×6.25) d.b.

2. The process of claim 1 wherein said acid insoluble solid material is optionally diluted and is dried to form the further non-soy oilseed protein product having a protein content of at least about 60 wt % (N×6.25) on a dry weight basis.

3. The process of claim 2 wherein the pH of the optionally diluted acid insoluble solid material is raised to a value selected from the group consisting of less than about 8.0 prior to the drying step.

4. The process of claim 2, wherein said acid insoluble solid material is washed by mixing with a quantity of water of about 1 to about 20 volumes of water, having a pH of about 1.5 to a value about 1 pH unit lower than the typical pH of isoelectric precipitation, then is separated from the wash water prior to optional dilution then drying steps.

5. The process of claim 4, wherein the pH of the optionally diluted washed acid insoluble material is raised to a value of less than about 8.0, prior to the drying step.

6. The process of claim 4 wherein the wash water is combined with the acidified soy protein solution of step (d) and processed as in at least one of steps (e)-(g).

7. The process of claim 2, wherein said acid insoluble solid material is simultaneously washed and adjusted in pH by mixing the acid insoluble solid material with a quantity of water of about 1 to about 20 volumes of water, and sufficient food grade alkali to raise the pH to a value of less than about 8.0, then is separated from the wash water by centrifugation, prior to optional dilution then drying steps.

8. The process of claim 7, wherein the optionally diluted simultaneously washed and pH adjusted acid insoluble solid material is further raised in pH as to a value of less than about 8.0, prior to the drying step.

9. The process of claim 2, 3, 4, 5, 7 or 8 wherein said acid insoluble solid material, diluted acid insoluble solid material, diluted washed acid insoluble solid material or diluted washed and pH adjusted acid insoluble solid material is pasteurized prior to drying.

10. The process of claim 9 wherein said pasteurization step is effected at a temperature and for a time selected of about 55° to about 85° C. for about 10 seconds to about 60 minutes.

11. The process of claim 1 wherein said extraction step (a) is effected at a temperature of about 1° to about 100° C.

12. The process of claim 1 wherein said water used for the extraction contains a pH adjusting agent so that the extraction is conducted at a pH of about 7 to about 8.5.

13. The process of claim 12 wherein the pH adjusting agent is selected from sodium hydroxide, potassium hydroxide and combinations thereof.

14. The process of claim 1 wherein said aqueous non-soy oilseed protein solution has a protein concentration of about 5 to about 50 g/L.

15. The process of claim 1 wherein said water for extraction contains an antioxidant.

16. The process of claim 1 wherein following said separation step (b) and prior to said acidification step (c), said aqueous non-soy oilseed protein solution is treated with an adsorbent to remove colour and/or odour compounds from the aqueous protein solution.

17. The process of claim 1 wherein said aqueous non-soy oilseed protein solution, after the separation step (b) and prior to the acidification step (c) is adjusted in temperature to a value of about 1 to about 35° C.

18. The process of claim 1 wherein the non-soy oilseed protein product is a canola protein product and the pH of said aqueous canola protein solution is adjusted in step (c) to about 1.5 to about 2.5.

19. The process of claim 1 wherein the non-soy oilseed protein product is a sunflower protein product and the pH of said aqueous sunflower protein solution is adjusted in step (c) to about 1.5 to about 3.5.

20. The process of claim 1 wherein the non-soy oilseed protein product is a hemp protein product and the pH of said aqueous hemp protein solution is adjusted in step (c) to about 1.5 to about 4.0.

21. The process of claim 1 wherein the non-soy oilseed protein product is a cottonseed protein product and the pH of said aqueous cottonseed protein solution is adjusted in step (c) to about 1.5 to about 3.0.

22. The process of claim 1 wherein the non-soy oilseed protein product is a flax/linseed protein product and the pH of said aqueous flax/linseed protein solution is adjusted in step (c) to about 1.5 to about 3.0.

23. The process of claim 1 wherein the non-soy oilseed protein product is a safflower protein product and the pH of said aqueous safflower protein solution is adjusted in step (c) to about 1.5 to about 4.0.

24. The process of claim 1 wherein the non-soy oilseed protein product is a sesame protein product and the pH of said aqueous sesame protein solution is adjusted in step (c) to about 1.5 to about 3.0.

25. The process of claim 1 wherein the non-soy oilseed protein product is a mustard protein product and the pH of said aqueous mustard protein solution is adjusted in step (c) to about 1.5 to about 4.0.

26. The process of claim 1 wherein the non-soy oilseed protein product is a peanut protein product and the pH of said aqueous peanut protein solution is adjusted in step (c) to about 1.5 to about 3.5.

27. The process of claim 1 wherein the pH of said aqueous non-soy oilseed protein solution is adjusted in step (c) to about 2.0 to about 2.5.

28. The process of claim 1 wherein said acidified aqueous non-soy oilseed protein solution following step (d) is subjected to a heat treatment step.

29. The process of claim 28 wherein the heat treatment step is effected to inactivate heat-labile anti-nutritional factors.

30. The process of claim 29 wherein the anti-nutritional factors are heat-labile trypsin inhibitors.

31. The process of claim 28 wherein the heat treatment step is effected to pasteurize the acidified aqueous protein solution.

32. The process of claim 28 wherein said heat treatment is effected at a temperature, and for a time, of about 70° to about 160° C. for about 10 seconds to about 60 minutes.

33. The process of claim 28 wherein the heat treated acidified non-soy oilseed protein solution is cooled to a temperature of about 2° to about 65° C.

34. The process of claim 1 wherein said acidified aqueous non-soy oilseed protein solution is dried to provide a non-soy oilseed protein product having a protein content of at least about 60 wt % (N×6.25) d.b.

35. The process of claim 1 wherein said acidified aqueous non-soy oilseed protein solution is subjected to concentrating step (e) to produce a concentrated acidified non-soy oilseed protein solution having a protein concentration of about 50 to about 300 g/L.

36. The process of claim 35 wherein said concentration step (e) is effected by ultrafiltration using a membrane having a molecular weight cut-off of about 1,000 to about 1,000,000 daltons.

37. The process of claim 1 or 35 wherein the acidified soy protein solution, partially concentrated acidified soy protein solution or concentrated acidified soy protein solution is subjected to diafiltering step (f).

38. The process of claim 36 wherein said diafiltration step (f) is effected using a diafiltration solution of water or acidified water.

39. The process of claim 38 wherein said diafiltration step (f) is effected using volumes of diafiltration solution of about 1 to about 40 volumes.

40. The process of claim 37 wherein said diafiltration step (f) is effected until no significant further quantities of contaminants or visible colour are present in the permeate.

41. The process of claim 37 wherein said diafiltration step (f) is effected until the retentate has been sufficiently purified so as to provide a non-soy oilseed protein isolate with a protein content of at least about 90 wt % (N×6.25) d.b.

42. The process of claim 37 wherein said diafiltration step (f) is effected using a membrane having a molecular weight cut-off of about 1,000 to about 100,000 daltons.

43. The process of claim 37 wherein an antioxidant is present in the diafiltration medium during at least part of the diafiltration step (f).

44. The process of claim 37 wherein said concentration step (e) and diafiltration step (f) are carried out at a temperature of about 2° to about 65° C.

45. The process of claim 37 wherein the partially concentrated or concentrated and/or diafiltered acidified non-soy oilseed protein solution is subjected to a heat treatment step.

46. The process of claim 45 wherein the heat treatment step is effected to inactivate heat-labile anti-nutritional factors.

47. The process of claim 46 wherein the heat-labile anti-nutritional factors are heat-labile trypsin inhibitors.

48. The process of claim 45 wherein said heat treatment is effected at a temperature and for a time of about 70° to about 160° C. for about 10 seconds to about 60 minutes.

49. The process of claim 45 wherein the heat treated non-soy oilseed protein solution is cooled to a temperature of about 2° to about 65° C.

50. The process of claim 37 wherein said concentrated and/or diafiltered acidified protein solution is treated with an adsorbent to remove colour and/or odour compounds.

51. The process of claim 37 wherein said concentrated and/or diafiltered acidified protein solution is pasteurized prior to drying.

52. The process of claim 51 wherein said pasteurization step is effected at a temperature and for a time of about 55° to about 85° C. for about 10 seconds to about 60 minutes.

53. The process of claim 41 wherein said concentrated and diafiltered acidified soy protein solution is subjected to drying step (g) to provide a non-soy oilseed protein isolate having a protein content of at least about 90 wt % (N×6.25) d.b.

54. The process of claim 1 wherein step e) and/or step f) is required and the pH of the concentrated and/or diafiltered acidified non-soy oilseed protein solution is raised to a value of less than about 8.0 prior to drying step (g).

55. The process of claim 37 wherein the concentration and/or diafiltration step are operated in a manner favourable to the removal of trypsin inhibitors.

56. The process of claim 1 wherein a reducing agent is present during the extraction step (a).

57. The process of claim 37 wherein a reducing agent is present during the concentration step (e) and/or the diafiltration step (f).

58. The process of claim 57 wherein the reducing agent is present to disrupt or rearrange the disulfide bonds of trypsin inhibitors to achieve a reduction in trypsin inhibitor activity.

59. The process of claim 1 wherein step e) and/or step f) is required and a reducing agent is added to the concentrated and/or diafiltered non-soy oilseed protein solution prior to the drying step (g) and/or the dried non-soy oilseed protein product.

60. The process of claim 59 wherein the reducing agent is added to disrupt or rearrange the disulfide bonds of trypsin inhibitors to achieve a reduction in trypsin inhibitor activity.

61. The process of claim 2, wherein said acid insoluble solid material is washed by mixing with a quantity of water of about 1 to about 20 volumes of water, having a pH about the same as the pH of the acid insoluble material, then is separated from the wash water prior to the drying steps.

* * * * *